(12) United States Patent
Epstein

(10) Patent No.: US 11,763,951 B2
(45) Date of Patent: Sep. 19, 2023

(54) SYSTEMS AND METHODS FOR TREATING PATIENTS MEDICALLY USING PATIENT DIRECTION WITH OPTIONAL PHYSICIAN COLLABORATION

(71) Applicant: Joseph Alan Epstein, Pleasanton, CA (US)

(72) Inventor: Joseph Alan Epstein, Pleasanton, CA (US)

( * ) Notice: Subject to any disclaimer, the term of this patent is extended or adjusted under 35 U.S.C. 154(b) by 42 days.

(21) Appl. No.: 16/826,227

(22) Filed: Mar. 21, 2020

(65) Prior Publication Data

US 2020/0303079 A1 Sep. 24, 2020

Related U.S. Application Data

(60) Provisional application No. 62/822,026, filed on Mar. 21, 2019.

(51) Int. Cl.
*G16H 50/30* (2018.01)
*G16H 10/60* (2018.01)
*G16H 20/00* (2018.01)
*G16H 80/00* (2018.01)

(52) U.S. Cl.
CPC ............. *G16H 50/30* (2018.01); *G16H 10/60* (2018.01); *G16H 20/00* (2018.01); *G16H 80/00* (2018.01)

(58) Field of Classification Search
CPC ........ G16H 10/60; G16H 20/00; G16H 50/30; G16H 80/00
USPC .......................................................... 705/3
See application file for complete search history.

(56) References Cited

U.S. PATENT DOCUMENTS

2004/0117215 A1* 6/2004 Marchosky ............ G16H 10/60
705/3
2004/0249778 A1* 12/2004 Iliff ........................ G16H 15/00
706/45

FOREIGN PATENT DOCUMENTS

WO WO-0208941 A1 * 1/2002 ......... G06F 19/3418

OTHER PUBLICATIONS

Ng, Roy K.; Privacy and Efficacy of Electronic Health Records (EHRs): A Triangulation Study in Ontario, Canada; The University of Manchester (United Kingdom). ProQuest Dissertations Publishing, 2019. 27798239. (Year: 2019).*

* cited by examiner

*Primary Examiner* — Hiep V Nguyen

(57) ABSTRACT

A method and system providing medical treatment to patients. In some embodiments, a patient is granted clinically sufficient access to their underlying health records and is able to observe and place treatment orders. In some embodiments, a patient and a practitioner are able to collaborate on the patient's treatments. In some embodiments, a practitioner is summoned from a pool of practitioners. In some embodiments, a change manager tracks changes to the underlying medical treatment plan for potential review, approval, modification, or rejection. Further embodiments provide a collaboration or supervision interface between patients and automated medical decision or practice systems, such as robodocs.

20 Claims, 14 Drawing Sheets

SYSTEMS AND METHODS FOR TREATING PATIENTS MEDICALLY USING PATIENT DIRECTION WITH OPTIONAL PHYSICIAN COLLABORATION

CROSS REFERENCE TO RELATED APPLICATION

This application claims the benefit of provisional patent application Ser. No. 62/822,026, filed Mar. 21, 2019 by the present inventor, the entire content of which is hereby incorporated by reference.

BACKGROUND OF THE INVENTION

1. Field of the Invention

The present invention relates to the field of practicing medicine on a patient, including the surrounding electronic records and treatment order systems.

2. Description of the Prior Art

Current approaches to medicine rely on the assumption of infallibility of physicians. However, physicians are subject to a number of cognitive biases and errors. A major source of error is that of the practitioner needing to personally feel responsible for delivering a cure—and thus, they wish to be seen as the healer, a modern-day shaman with the answers to the patient's problems. This very human error often leads to self-reinforcing confirmation bias, as practitioners with lower than expected hit rates "eat their errors", by ignoring the failings or attributing them to other means beyond their control, while overlearning from successful resolutions, even those that may have resolved on their own without intervention. Unfortunately, the predictableness of the bias leads to a fairly predictable outcome: a physician's truest wish is that her patient be compliant, to be the canvas so that her brushstrokes can accurately be reflected, so that she may get onto the important work of being doctor, healer.

This is no idle concern. The opioid epidemic was caused, in principal part, by this self-reinforcing error. Opioids were never appropriate first-line treatments for common pain from physical injury. However, initially triggered by a poorly done medical report taken out of context, practitioners began prescribing opioids to treat injury without regard to the addictive potential that was well understood. The self-reinforcing cycle created was that opioids are effective short-term treatments for pain, but are extraordinarily damaging when used long term. A physician with a patient in pain, however, felt tremendous pressure to prescribe opioids once a sufficient number of peer physicians were prescribing as well, based on the simultaneous desire to make a positive impact on the patient and the fear of being in the minority by withholding effective treatment and possibly violating the oath to do no harm. To withhold opioids was to personally accept failure to treat, even though the correct answer was to withhold.

This cycle exists in multiple places in the treatment regime. Because specialists see the world through the lenses of their specialties, specialists are liable to have a greater false positive rate than expected. Specialists have a self-selected population: most patients do not seek out specialists unless they suspect or are suspected of having a condition the specialist can treat. Therefore, a specialist can have an artificially high true positive rate by biasing their evaluations towards the positive over and above what the true prevalence is. Taken extremely: say a headache specialist existed, and set up a headache clinic, where every patient—without regard to their true condition—is given two ibuprofen. This clinic will have an unusually high success rate, even though all patients who suffer from more severe conditions that ibuprofen will not treat will continue to suffer, or perhaps die.

Intervention biases come about often because our current medical system does not treat the patient as an equal to the physician. The patient is more likely to know where they suffer—even if they do not know why—and whether a treatment is working. The patient is likely to know that their headache has not been relieved—even if the physician has inadvertently become biased towards their treatment, given that their own survey of their practice shows tremendous efficacy. However, the culture of medicine has had centuries to be locked into sense of doctor-as-healer, and thus has built tremendous resistance to patients being on an equal footing.

FIG. 1 (prior art) demonstrates how this has forced the technology of modern medicine down the wrong path. Patients 100 today are allowed to access, at best, a patient health portal 190 (such as Epic System's MyChart), which is designed to provide—by way of a function of severe redaction—a minimalistic view into the treatment system that the practitioner 170 has full control of Patients may be able to see occasional "safe for patient viewing" notes, as well as lab test results which were published to them; they may pay bills, schedule appointments, and even request refills. But they are not provided actual access to their health records—even though HIPAA mandates it—and, should they wish to be informed, they are required to submit a paper request to a medical records office, who will then flood them with paper printouts containing nearly incomprehensible medical terms. This use of a portal is one way that the provider redacts the medical record. In other words, the system is designed, and designed well, to manage patient medical care and information as if they were state secrets going through a Freedom of Information Act review process for scrubbing and blacking out. The patient is not provided clinically sufficient information about their condition. Instead, often only whatever the practitioner, practice, or electronic portal designer deemed to be useful without causing stress to the patient is presented. In this method, one might regard the patient as the product and not the customer: rather, the payor (such as insurance) is the real customer. Remember, the very language underlying the practice of medicine was constructed as much as an obscure shibboleth to identify and protect a physician and avoid revealing "too much" to the patient as was it a way to allow for consistent communication to prevent error by colloquialism. (Using "recipe", now abbreviated Rx, for a prescription is a glaring example, recipe in Latin meaning the command for you, the pharmacist and not the patient, to take the included list and make something out of it to then serve. We still use the word for in the same way today for food recipes.)

There has been hope that computers can automate away biases. It is famously known that computers can often diagnose better, given a list of symptoms, than a human. However, automated treatment is not a solution. To begin with, machine learning algorithms have no knowledge of science. Instead, they are trained on typical expert behavior, and thus are doomed to replicate whatever errors the humans they were trained on have. A properly operational expert system trained on electronic health record (EHR) treatment data for physical pain would immediately replicate the overprescribing of opioids. All statistical models would, by design. The biases computers eliminate are merely that of the regard to the specific patient, and not those of the physicians in general towards their own practice. Moreover, computers are not licensed physicians, and thus cannot practice in most states. This is unlikely to change. Unlike with self-driving cars, the liability scheme for medical malpractice is rich and intentional, and bypassing it is inappropriate at best.

SUMMARY

In accordance with some embodiments, a method and system for delivering medical treatment to patients, thus causing their conditions to be altered in physically manifested ways, by allowing patients to access their full medical records and participate in the orders for treatment. In some embodiments, a patient and practitioner collaborate to determine a course of treatment. In some embodiments, the systems operate on an electronic health record and treatment scheme. In some embodiments, an automated robodoc is present.

DETAILED DESCRIPTION

Figure 1:
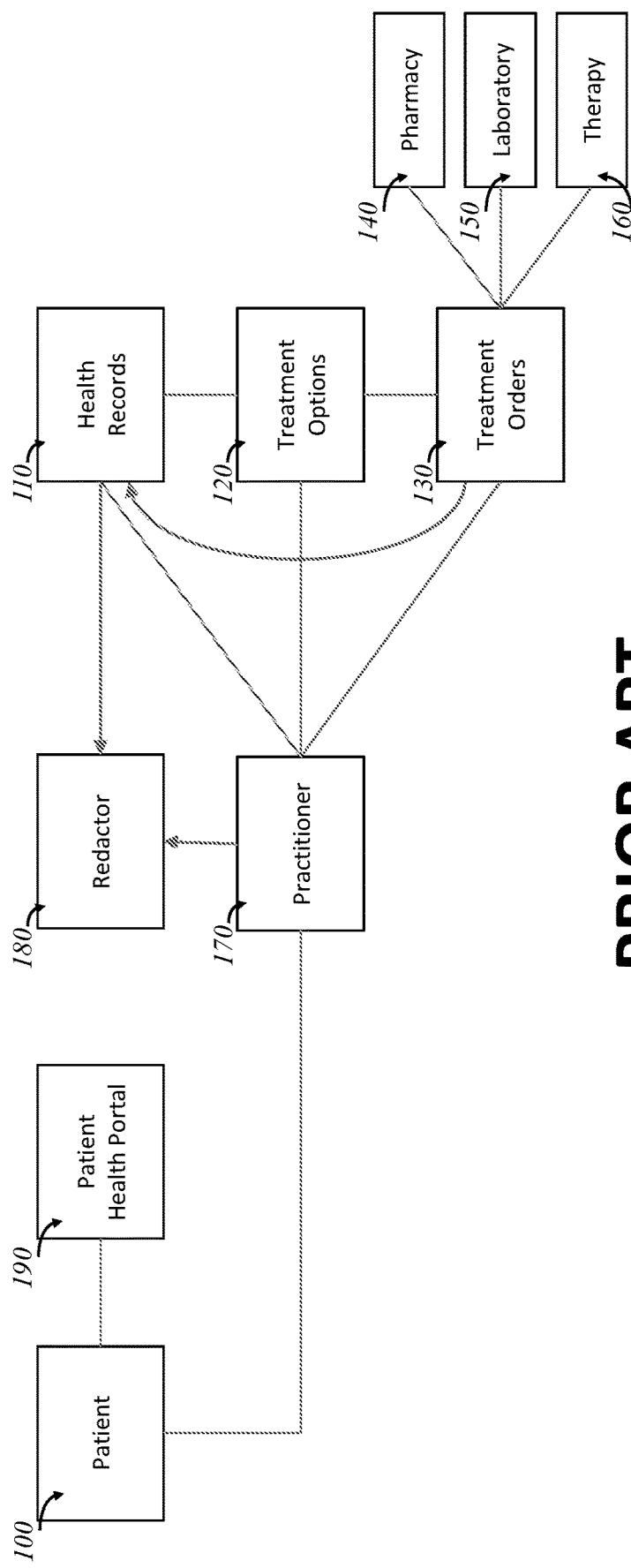
FIG. 1 is a diagram of prior art, showing how patients are directed to a health portal that uses a redaction function to restrict access to the patient's true health information, while allowing the practitioner full access.
Figure 2:
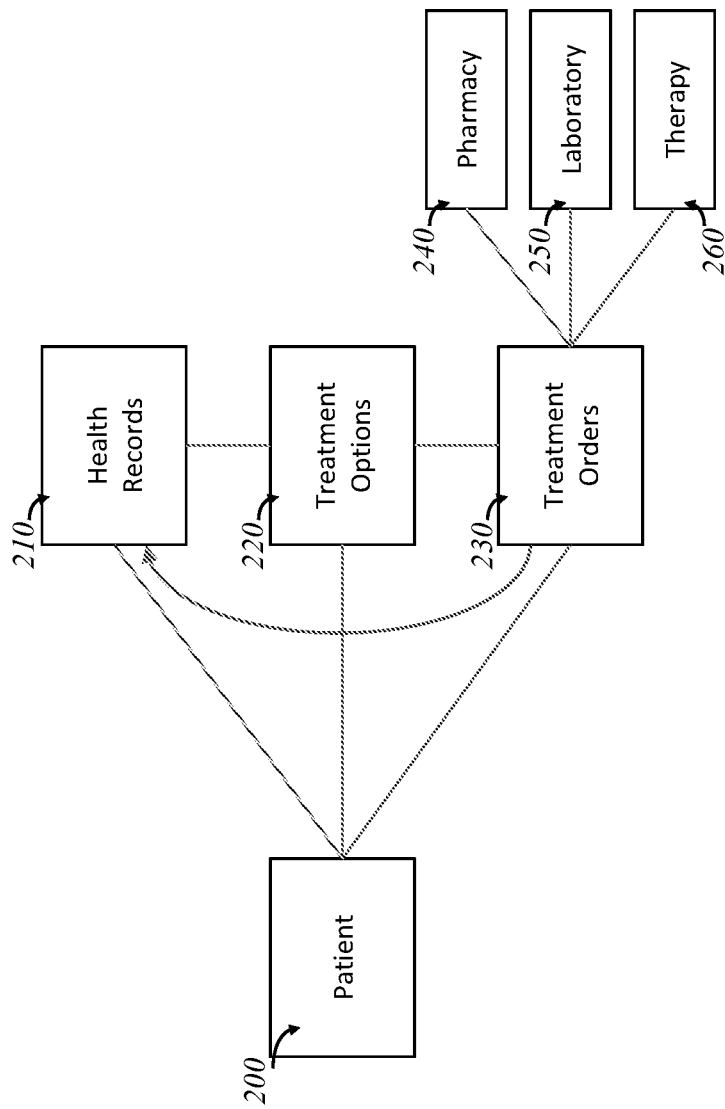
FIG. 2 is a diagram of an embodiment of the invention, showing a patient having access to treatment orders and his health record.

Disclosed are new methods for practicing medicine, for delivering medical treatments, and for building electronic tools that are fundamental to that practice. FIG. 2 discloses an architecture for delivering patient directed medicine as per some embodiments of the present invention. Patient directed medicine is a form of medical practice and medical treatment, designed to create a change in the patient, where the patient may be able to be entirely informed of, consenting of, and expected to partake in the practice of their medical care. Although the following list are not requirements—as in compromises or differences do exist for each point and the points are not limiting—this type of medical treatment as disclosed tends to have the following features:

1. The EHR and treatment availability are often condensed into one tool or application, or a cohesive suite of them.
2. The tool is designed for the patient to use.
3. The patient has clinically sufficient access to the information within in the tool concerning their own medicine, at least as complete as a physician would or should for the scenario.
4. The tool delivers real medical treatment: prescriptions, tests, and interventions are ordered through the tool (directly or indirectly).

Patient 200 has clinically sufficient access to health records 210, around which she can use to evaluate the treatment options 220 and place orders 230, such orders to entities such as a pharmacy 240, laboratory 250, and hands-on therapy providers 260 (such as physical therapists). The health records 210 will be updated with the ordered treatments 230, as well as the results as they come in. For these embodiments, said clinically sufficient access may be direct or indirect, through one or more steps, and may have additional information or context presented alongside or within the means of access, but for a given set of treatment options under consideration (including the null option of not treating), all available medically relevant data necessary for a competent practitioner to typically make clinically appropriate decisions is made available to patient 200. This does not require all information necessary to confidently make a decision to be made available, because that information may not in fact exist or may be of too low quality to provide competently, as medicine operates with some degree of uncertainty. Furthermore, extraneous or distracting information may be held back or put out of the way, as the standard here is what a typical clinical assessment would require, and reasonable attempts to hold back the firehose of information are acceptable. Clinically sufficient need not be unbiased. As well, not all medical information need always be given; the system need not provide for every possible treatment class, but can be limited to a specific focus area and keep the rest aside. (For example, one embodiment applies the methods to produce a system for treatment of minor dermatological conditions, but holds back choices for melanoma treatment and may instead refer the patient directly in for a consult with a physician in a more typical setting. Furthermore, such a system need not provide cardiac information which is not relevant to the treatment of minor dermatological conditions.)

To this, many embodiments add a fifth trait:

5. Licensed professionals can confirm and perform quality control over the treatment.

This last rule is useful where only licensed professionals may order certain tests, prescriptions, and treatments. In those cases, the licensed professionals are, in a legal sense, in fact the ones to have practiced the medicine that the patient has entered, as the patient may be said legally to be merely making a suggestion which a licensed practitioner confirms or denies. That being said, this fifth trait may be useful outside of licensing reasons, as will be explained in detail below.

Figure 3:
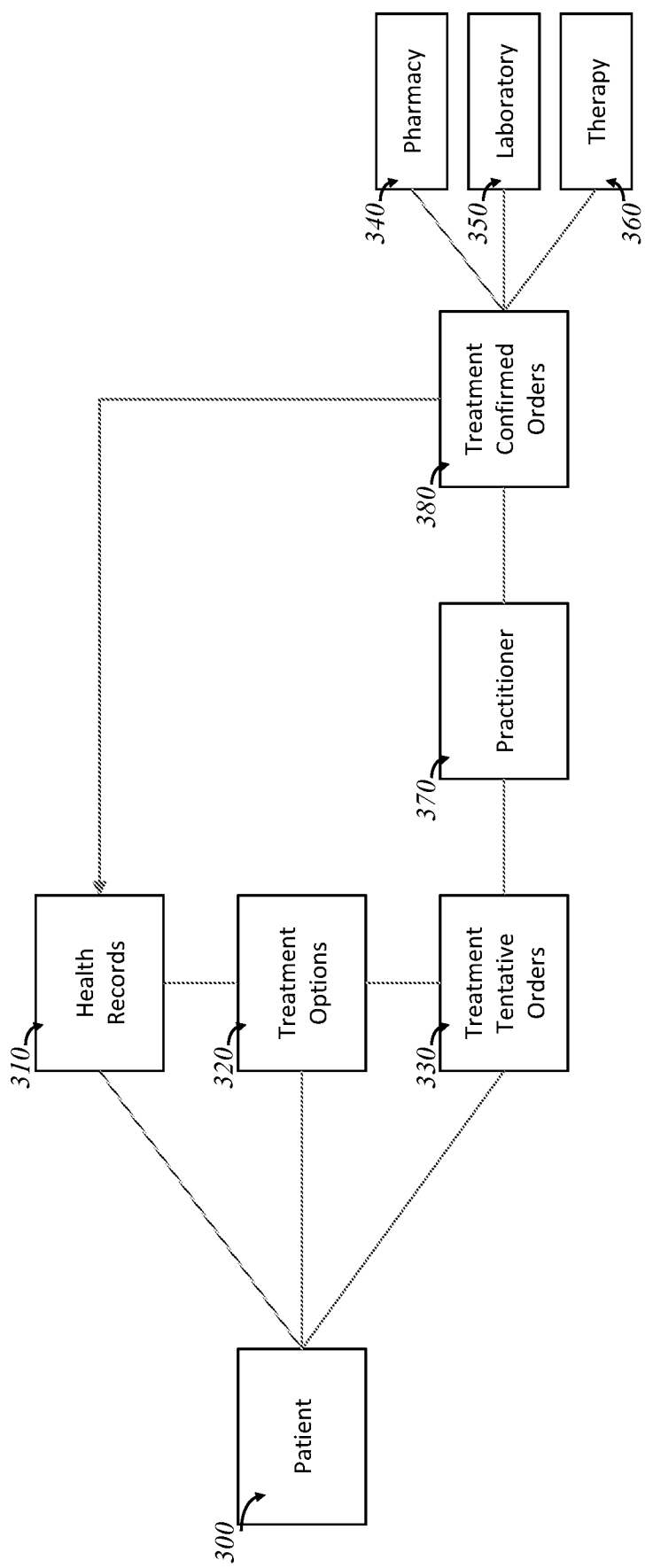
FIG. 3 is a diagram of an embodiment of the invention, showing a supervising practitioner who confirms treatment orders, with or without modification.

FIG. 3 shows some embodiments with the practitioner inserted into the process as above. In these embodiments, a patient 300 sees her record 310 and chooses from treatment options 320, which are then dispatched to a practitioner 370 for the practitioner to confirm (or not if the order is inappropriate in her professional opinion): confirmed orders 380 are sent on to take effect.

Substituting a practitioner with a patient is a surprising mode of operation, and thus belies a new invention. But how can this work? The patient is not expected to be a physician, so how can he be expected to pilot the plane, so to speak, as an untrained passenger? For many embodiments, the answer lies in the changes that must be made to the operation and use of the principal medical delivery blocks (EHR, Treatment Options, Orders).

Figure 4:
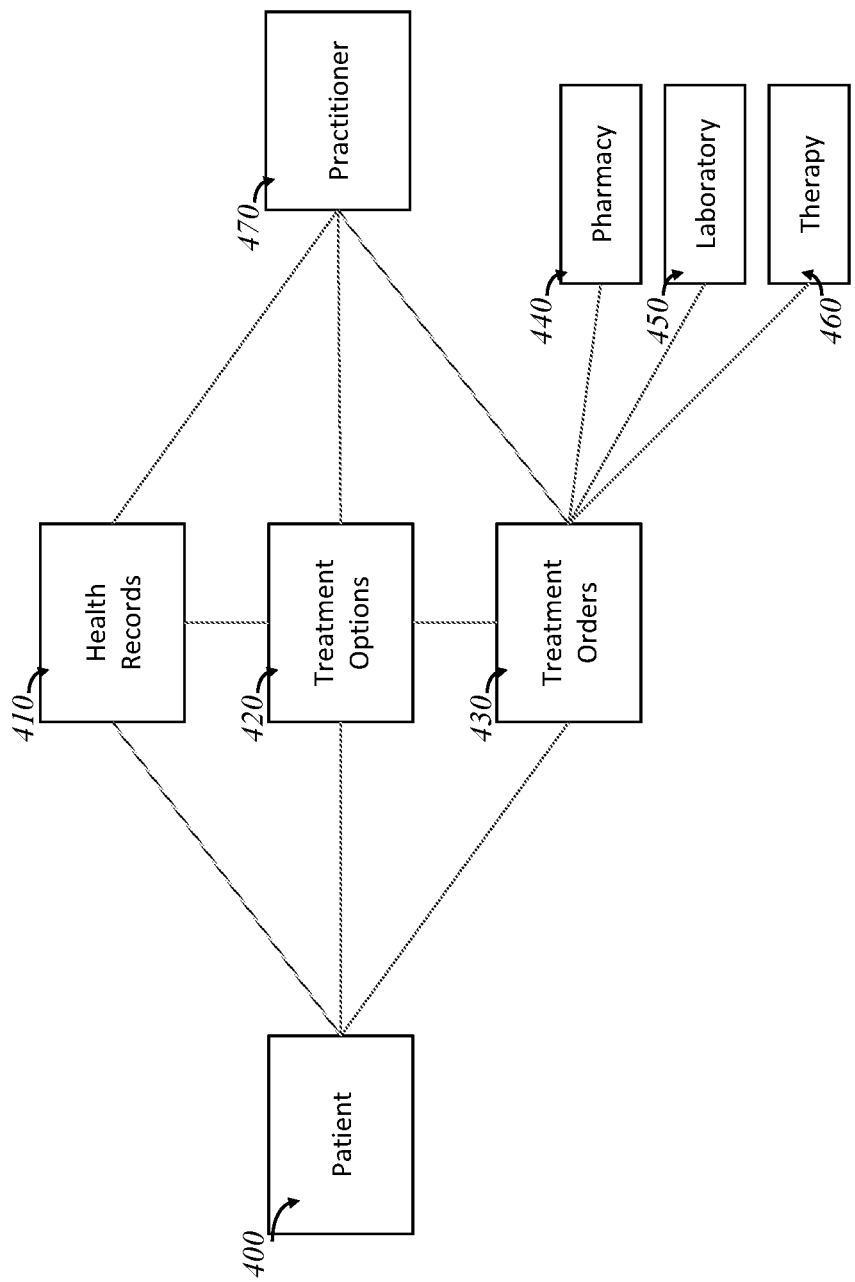
FIG. 4 is a diagram of an embodiment of the invention, showing a practitioner and a patient with similar structural access to a treatment system.

Collaboration between a patient and a practitioner is one method of solving that, much the same as how student drivers have a dual steering wheel into the car with the trainer able to operate the car if needed without changing seats. FIG. 4 shows a collaborative architecture as used in some embodiments. Here, a practitioner 470 and patient 400 are able to interface into the same sets of records 410, options 420, and orders 430. This, at a root level, allows for the practitioner to guide the patient through the treatment evaluation process, because they both can see the same system. (Note that although only one patient and practitioner is shown, multiple ones may be present, and in different use cases the patient may be substituted with another collaborative or supervised entity.)

Figure 5:
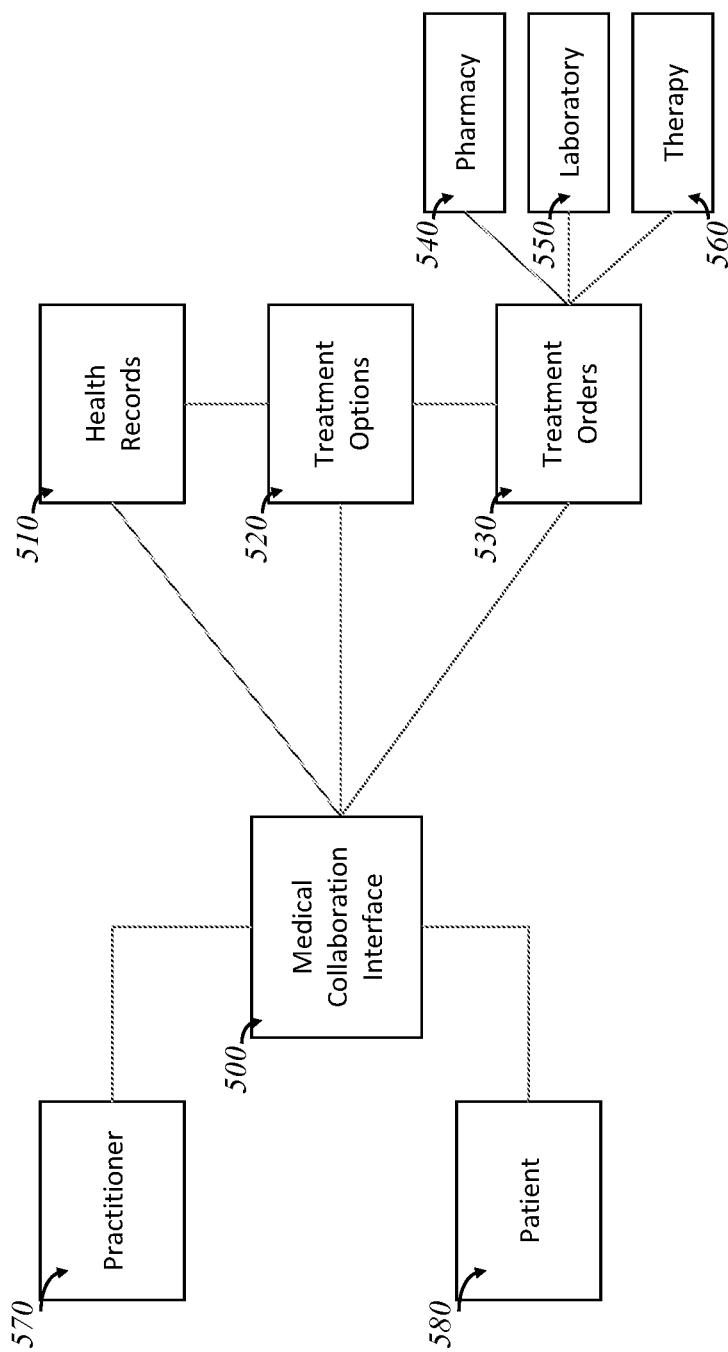
FIG. 5 is a diagram of an embodiment of the invention, showing a practitioner and patient collaborating through a medical collaboration interface into a treatment system.

FIG. 5 shows some embodiments with a Medical Collaboration Interface 500. The medical collaboration interface 500 is a sharable resource, which gathers the information from health records 510 and treatment options 520, and provides both a practitioner 570 and patient 580 one or more screens of an application that allows them to interact. The medical collaboration interface 500 can then place orders 530 or make alterations to the health records 510.

The value of this is that the patient and practitioner can sit, locally or remotely, looking at the same electronic interfaces. In some embodiments, the interfaces are screen shares, meaning that the patient and practitioner are both viewing one instance of a user interface—such as using remote desktop protocols and viewers—and any change made in one can be made in another. In some embodiments, the users see each other's mouse pointers or pointing devices. They may also see the same user interface blocks. When one user makes a change to the user interface, the other ones may see those changes in real time. In some embodiments, those changes are highlighted to stand out. In some embodiments, users typing see carats with the active user's name on it as the typing occurs as well. The goal here is to draw the user's attention to the changes being made: in some ways, this is similar to online collaborative office products (such as Google Docs or Sheets), but the interface being used is no ordinary office document but a medical system that can and does make life and death decisions.

Figure 6:
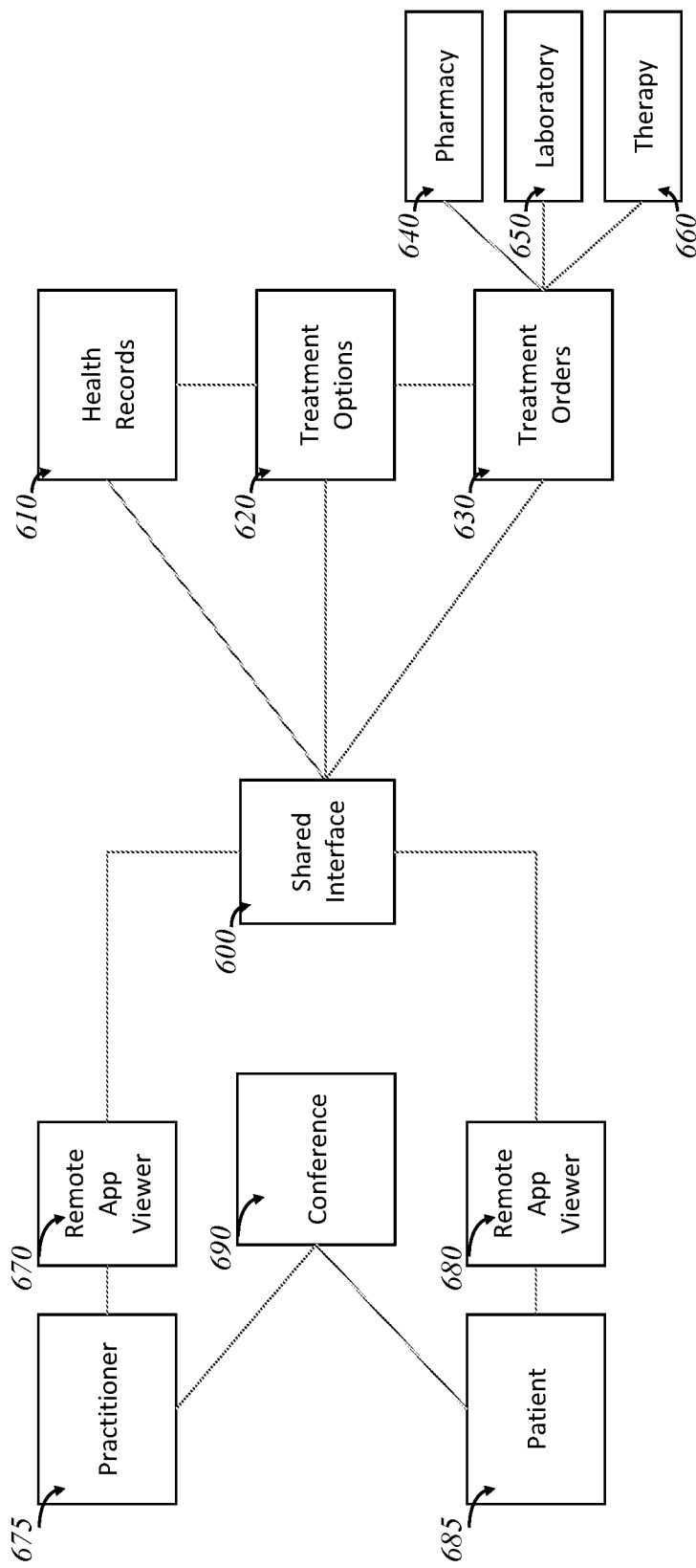
FIG. 6 is a diagram of an embodiment of the invention, showing a practitioner and patient using a common shared user interface into a treatment system, both users tied together in a conference.

FIG. 6 discloses, in some embodiments, a practitioner 675 and patient 685 sharing a conference 690, which in some cases is a full teleconference with remote audio as well as a shared desktop. In this way, the practitioner 675 can highlight what's on the interface to the patient 685, such as a choice of treatments 620 and which one they're currently looking at, and walk the patient through what is being offered. In some embodiments, the conferencing block 690 performs audio conferencing. In some embodiments, it performs real-time messaging, such as chatting or texting. In some embodiments, the conferencing 690 is offline capable, and stores messages for later reading, such as email or unread texts.

Figure 7:
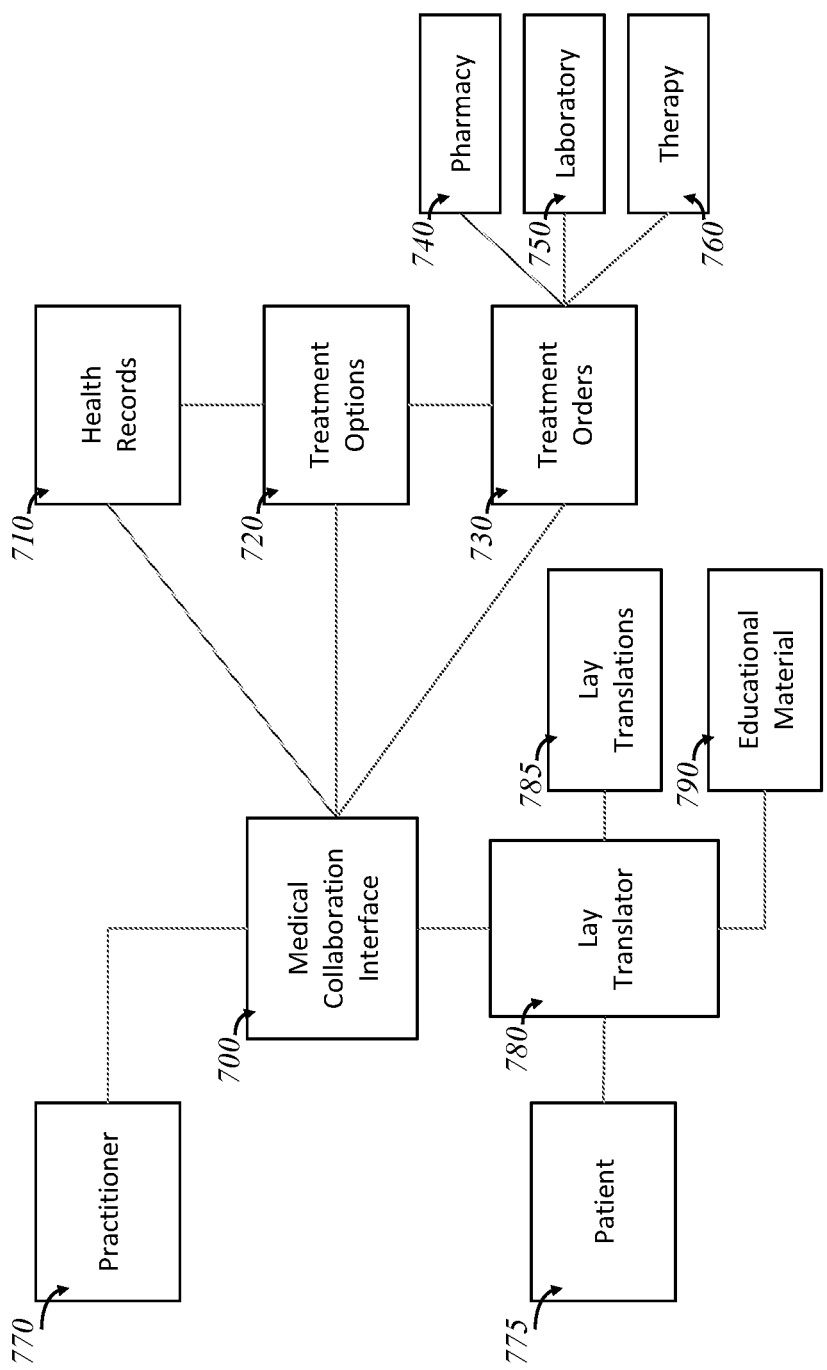
FIG. 7 is a diagram of an embodiment of the invention, showing a lay translator and educational material provided to the patient to assist the patient's understanding of the medical situation.

Furthermore, although the patient and practitioner may see the same information semantics on the screen, they may have different needs for terminology. FIG. 7 shows some embodiments with an ability to perform lay translation. The concept here is that a clinician and a layperson may have different needs for the words they see on the screen, but may still wish to have shared access to the same user interface. For example, a practitioner 770 may want to see "myocardial infarction"; a layperson 775 "heart attack". In these embodiments, a lay translator 780 makes that substitution by accessing appropriate translations 785, which in some embodiments may be a medical dictionary. Some embodiments use access to the syntactic structure of the interface and the written content to replace the words: one such embodiment relies on HTML interfaces and makes word substitutions. In some embodiments, the substitution and its original are both shown, such as through active regions, tooltips, parenthetical comments, or sidebars. In some embodiments, the user can control the degree of translation (or dumbing down) they wish to see. This need not be limited to words. A physician may wish to enter an order for medication in mg/kg; another user (a pharmacist, say) may wish to see it in prescriptible form, such as number of pills of a bottle at a specified mg with the patient's weight, known by the EHR, automatically translated. This shows a semantic translation, which has the value of allowing users to choose the manner of their own interface and its semantic approach while still allowing the user to see meaningful changes made by others. It's important to note that the change highlighting aspect need not be applied real time: changes may be marked for later review and/or approval, such as in concert with what is disclosed below.

Furthermore, some embodiments provide educational material 790 to certain users, based on context or need. These users need not be patients: this has value for physicians as well; the figure shows the patient application embodiments but it is understood that other users can be connected in slot 775 and make use of the educational materials as well, and that the materials can be per user based on the audience and need and need not be the same for all. The educational materials in some embodiments are precise and made available only by scope. In some embodiments, the materials are wide-ranging. Some embodiments employ a WebMD-like system of information, where medically curated articles are indexed by condition, symptom, or concept. Some embodiments employ a wiki. Some embodiments refer to the content of diagnostic manuals. Some embodiments provide access to videos or handcrafted lessons to teach the patient what the process even is or what it means. This matchmaking of educational information to the patient based on need and context is quite powerful and can allow for greater patient satisfaction and more self-service operating time with the patient without needing as much (or any) online or laborious supervision by a practitioner.

Of course, the patient and physician need not always be on at the same time. In any embodiments, it is the point that the patient can be on at any time, and can explore the system as needed. For that end, many embodiments enable the practitioner to potentially adopt the role of as-needed concierge, being brought in at the appropriate part of the workflow, or at the patient's request, or even at the practitioner's own volition.

Figure 8:
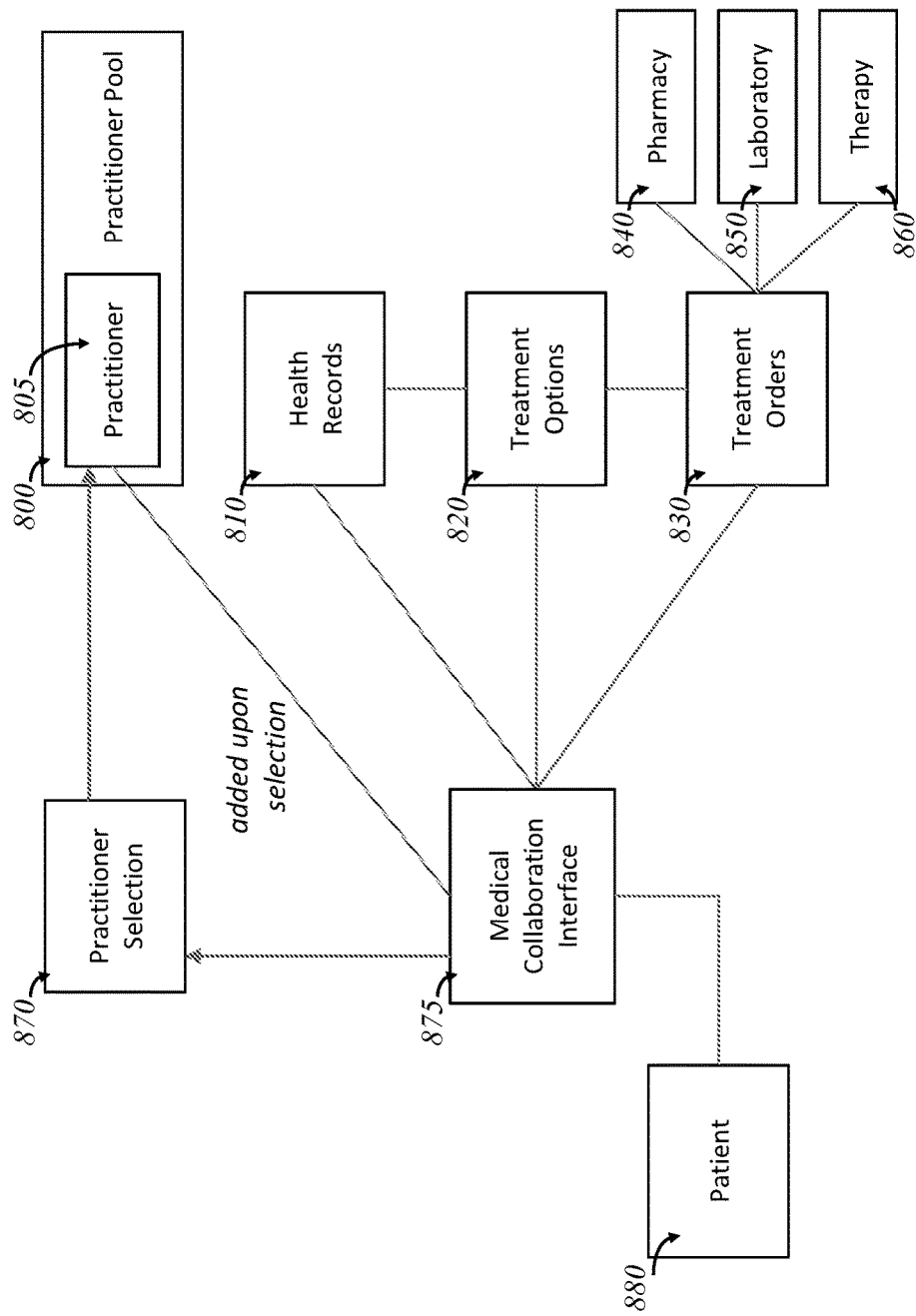
FIG. 8 is a diagram of an embodiment of the invention, showing a practitioner being selected from a pool of available and appropriate practitioners, to then be able to engage in using a medical collaboration interface.

FIG. 8 shows some embodiments that provide a method for dynamically requesting one or more practitioners to join in a session with the patient. Upon the appropriate trigger, a Practitioner Selection 870 (also called a practitioner selector) is invoked, which finds practitioner(s) 805 from a pool 800 and invites or request them to join into the medical collaboration interface 875. In some embodiments, the appropriate trigger is a request by the patient 880. In some, it is based on the workflow, such as if an order requires approval, or if the diagnosis is considered more risky or in need of professional assistance (such as bad prognoses like cancer or difficulty in laypeople's expected ability to understand like multiple scleroses). In some, it is based on real time or past events (the availability of a test result, the retroactive processing of health information such as new indications from prior data based on new research). In some, it is based on availability of additional services or their funding: a patient has a subscription to a premium support package; the patient's insurance will pay for guidance or counseling for the particular patient at this stage. The practitioner or practitioners 805 are selected from one or more pools 800. In some embodiments, the practitioner is selected based on their match with the patient. In further embodiments, this match is based on their skill or certification or measured quality level for the particular need of the patient, or the particular part of the workflow. In some embodiments, the practitioner is selected based on her cost structure or ability to earn. In some further embodiments, the practitioners are selected based on their billing rates, which are then provided to the patient so that the patient can see and/or choose practitioners based on the expected costs. In some embodiments, the system calculates those expected costs, taking into account likely duration of encounter if relevant or fixed-per-encounter costs, thus creating a two-sided marketplace whereby patients can shop for practitioners per-encounter and optimize according to their own criteria or the criteria they provide to the selection. In some embodiments, the practitioner is selected based on the subscriptions or programs or entitlements owed to or available for the patient. In some embodiments, the practitioner is selected based on the preference of the patient. In some, the selection is based on the prior relationship between the patient and practitioner. In some, the selection is based on quality score, such as a star rating. In some, the selection is based on the practitioner's ability to get up to speed for the case and/or at that moment. In some embodiments, the practitioner is chosen based on availability and quality of means of access to the system (landline better than cell, for example). In some embodiments, the practitioner is chosen based on location. In some embodiments, a utility function is used to weigh multiple such variables. Note that the request may occur in real time, or it may be deferred. And so it is with the collaboration: the collaborators may join immediately, or they may participate off-line. Some embodiments allow the users to express their desires or their mandates for the form of collaboration.

Figure 9:
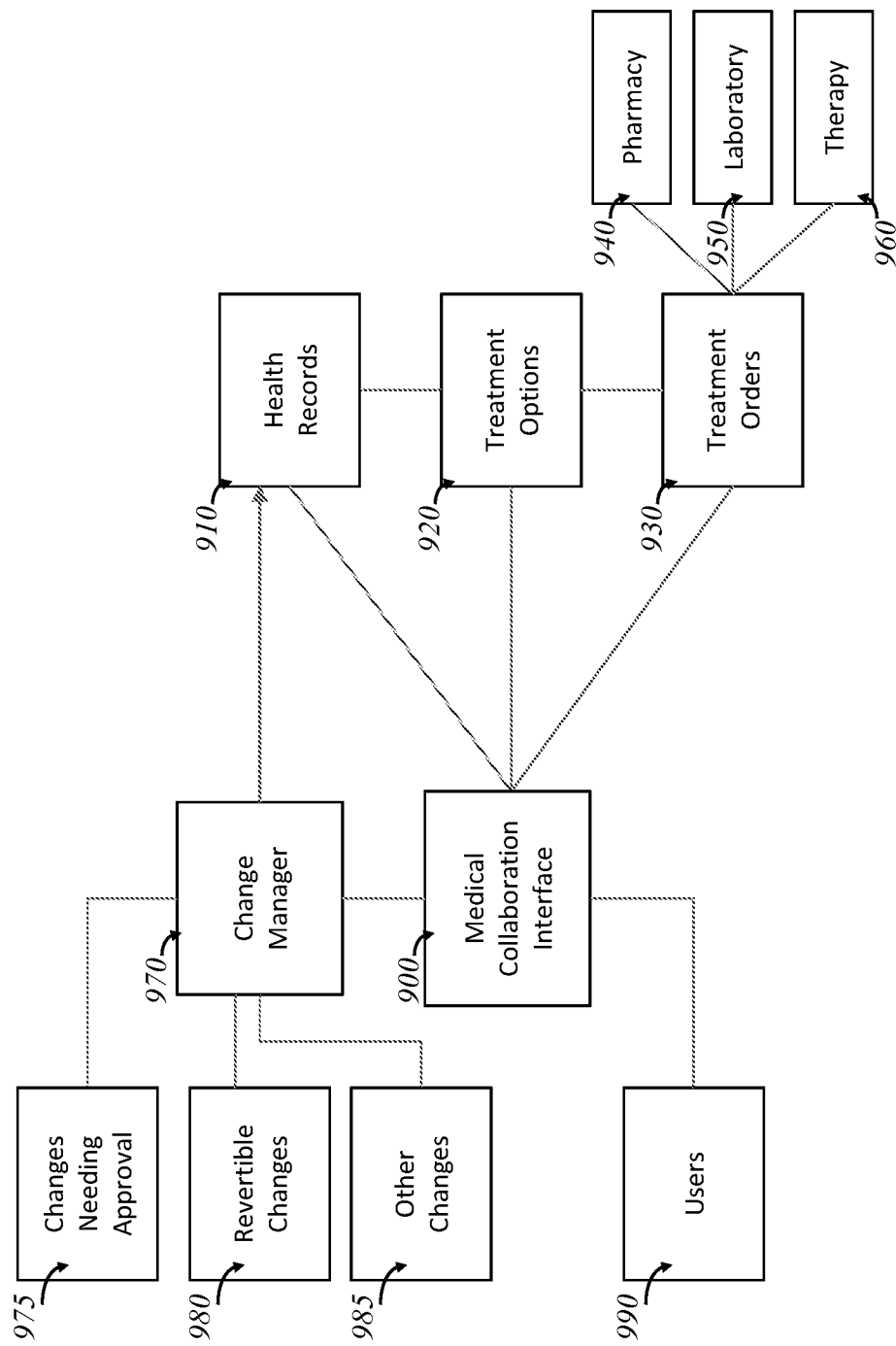
FIG. 9 is a diagram of an embodiment of the invention, showing a change manager interfacing with a medical collaboration interface.

To ensure collaboration and informed consent, some embodiments make use of a more aggressive form of ensured understanding FIG. 9 shows some embodiments with change management. A change manager 970 tracks the changes to a collaboration interface 900—and thus the changes to health records 910, treatment options 920, and orders 930. In some embodiments, some changes 975 are held in abeyance pending approval. In some embodiments, some changes 980 are revertible and can be backed out from the underlying system. Some changes 985 fit neither model. The change manager provides the opportunity for the necessary users to see and approve changes. The change manager in some embodiments possesses the logic for what workflows need approval or can be reverted, and the workflows and requirements for backing out or approving and furthering on the changes. Sometimes, the only approval will need to be for some users to see and confirm that they saw the change. Sometimes, the approval will require active effort, such as clicking on a box saying "I approve". Sometimes, the approval will require a signature. Sometimes, the approval will not be given, and the change manager will either revert changes or drop pending changes held in abeyance. In some embodiments, the change manager is implemented in a transactional manner, and can perform commits and rollbacks of state, either within itself or in conjunction with the underlying records and orders. In some embodiments, changes are stored as formal change orders; in some embodiments they are stored and presented fine-grained.

One possible use of these embodiments is to construct a method of approvals. One may require physician approval for all things required by law or license, in which case the configuration of the previously disclosed embodiment reflects an operation similar to that described in FIG. 3. Moreover, this provides an opportunity for the practitioner to become the licensed physician of record. However, one may also require patient approval for all things, in which case the system is now providing for completely informed consent: the patient need not accept any aspect of the changes, where the changes clearly are the language of medicine, or may pick and choose and send comments back through change management or request collaboration such as in FIG. 8, again either real time or through an off-line communication. Note that the rules for approvals need not be uniform or the same across all changes, but are expected usually to be both specific to the change and based on the regulatory, insurance, or patient requirements and needs. In some embodiments, for example, the patient has the ability to require his confirmation for everything but the practitioner's only on those that are required by law or insurance. In some embodiments, a practitioner or other user can create a one-off requirement for approval, such as to record patient consent very explicitly, such as for risky procedures. In some embodiments, multiple phases of approvals are able to be established. In some embodiments the requirements for approval or review are implemented using a rules engine. Notice how in many of the embodiments the workflow takes on the characteristics of an engineering code review.

One possible advantage of requiring this sort of patient participation is that it may lead to better adherence. For example, type 2 diabetes is famously a disease of adherence. If patients merely stopped their profligate ways, one might say unkindly, they would be cured of the disorder. And this is a true statement in many cases, but type 2 diabetes and lifestyles that lead to it are notoriously difficult to modify, usually because of psychological, social, economic, or other medical reasons that force the patient into a set of limited choices much smaller than that for which a practitioner would hope. However, providing the ability for patients to interact with, sign off on, and even author their own treatment this way may increase the psychological stakes and involvement for the patient. Moreover, it may even increase their sense of teamwork with the other users, and thus create a bond and a social framework for solving the problem. After all, if a doctor-knows-best physician tells you to lose weight, it's no different than a mother-knows-best parent telling a teenager to clean her room. But if a doctor as a teammate works with a patient and together they realize that the patient wants to lose weight, then it is no different than a boyfriend coming over giving the teenager a good personal reason to want to clean her room. A platform that replaces the existing doctor/patient relationship creates fertile ground to rebuild a new one, perhaps a stronger one forged in trust and openness rather than force and shame.

Note that the practitioner here is any person or thing that can practice or participate with the practice of medicine. It may be an M.D., a nurse practitioner, a regular nurse, a robodoc, or even a totally unlicensed person in cases and for purposes where the workflow at hand does not require a license. The practitioner selection is capable, in many embodiments, of determining this requirement and making the match; and again, the match may be per condition or workflow or instance or time and need not be the same agent every time, even for the same condition. The practitioners may exist in a real or virtual call center, and whoever is next available gets rung, for example.

One of the more powerful aspects of some embodiments of the present invention is that the patient can be on any time, with or without any sort of collaborator. This creates an opportunity for a patient to have the ability to understand what their situation is, to see what all the possibilities are for both diagnoses and treatments, and to test out possibilities by trial and error, to see a system where the patient can explore the history and decisions.

Figure 10:
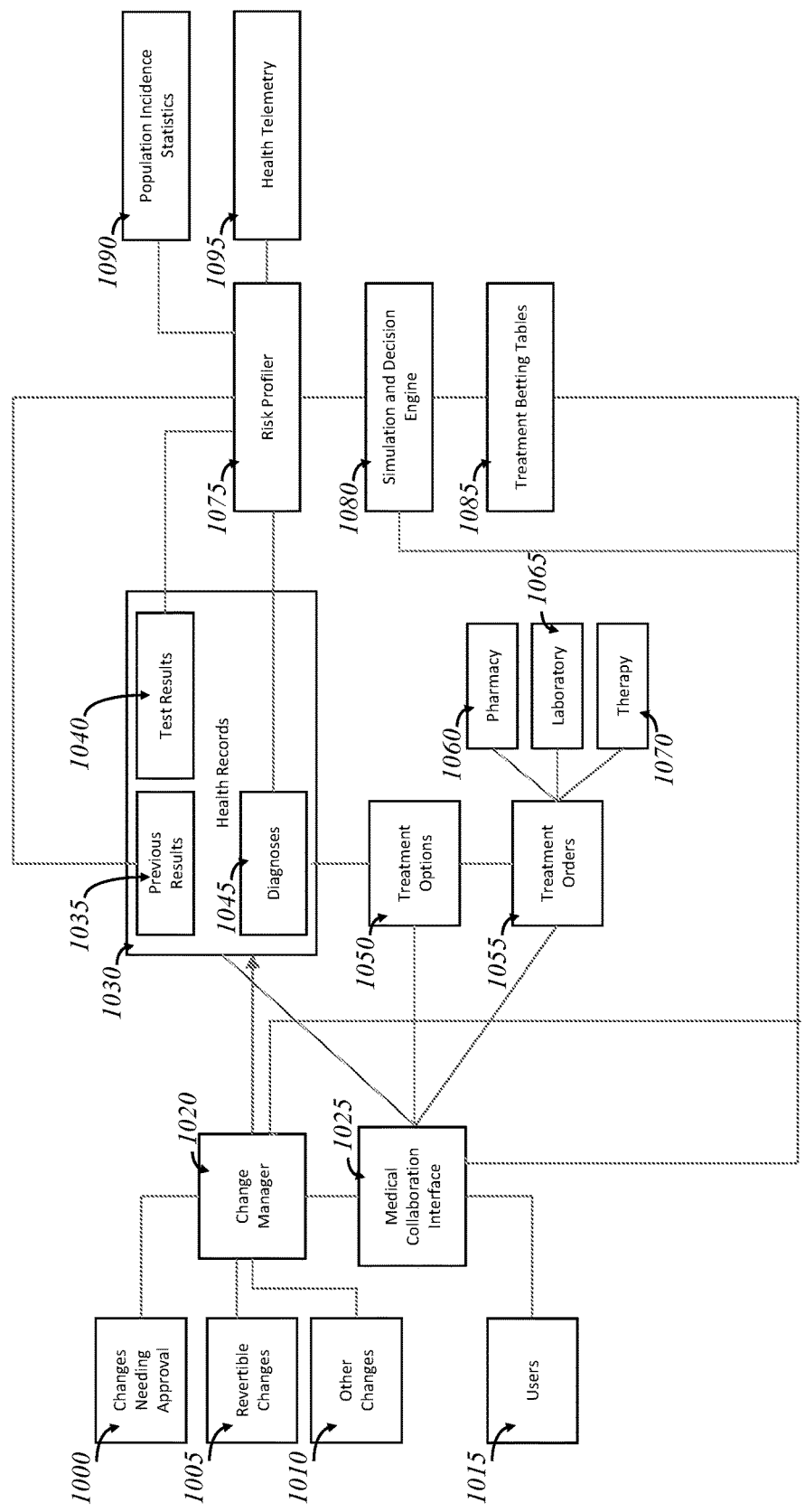
FIG. 10 is a diagram of an embodiment of the invention, showing an integration of collaboration and health records with a risk profiler and simulation and decision engine.

A novel integration of the present invention is possible with that of some embodiments of the invention disclosed in application Ser. No. 16/751,069, the entirety of which is hereby incorporated by reference. Within that application, embodiments of an invention are disclosed which use decision support and simulation, including having a patient and physician both use some embodiments (such as that disclosure's FIG. 7). FIG. 10 of the present disclosure shows some embodiments with a simulation and decision engine 1080 integrated into a medical collaboration interface 1025 alongside change management 1020. This combination creates a way for users to create one or more treatment simulations based on a risk profile generated by profiler 1075 and medical history of the patient and then enter it into the change manager 1020 for users to compare, contrast, collaborate, comment, and commit or cancel as needed. Imagine a patient has lost 30 pounds in a month on an unexpectedly successful diet. This information is available to the risk profiler 1075, which can use its population statistics 1090 to predict that gallstones is a possibility, and in the search across potential future patient paths and treatments it may also detect that the incidence rate is brought down significantly by the administration of bile acids, such as ursodiol. In the embodiments being discussed, the administration of prescription ursodiol, and a similar one of nonprescription bile acids—both being treatment options 1050—may then fed to the change manager and introduced as a possible change, reviewed by nobody yet. In these embodiments, the simulation and decision engine, running autonomously to determine possible future paths that reduce risk, introduces the alternatives into the collaboration interface. In some embodiments, the options enter via side panels or other methods not directly into the change manager to establish that the option is available. In some embodiments, a subset or the full set of possibilities is entered into the change manager, as in the example above. Further embodiments pick that subset based on factors such as cost, speed, ease of use, relevance, availability, efficacy, and other medical or practical information. Continuing the example, the users can now observe the new suggestions, and simulate what the outcomes will likely be using 1080. In this example, the difference is likely to be minor, as the prior odds of having gallstones is high but not dominating because of the weight loss. The users may now start pegging prior probabilities by shifting further down the paths of conditional probabilities, such as establishing the simulated prior of gallstones at 1 to see what the best treatment would then be. Perhaps, for the patient in this example, the patient is travelling and is not near a pharmacy or has no pharmacy benefit, and thus ursodiol is not available easily, but bovine bile supplements are. Then the users can agree (based on the agreement rules if present) to proceed to the administration of OTC bile acids. Or perhaps the opposite is true, and only the prescription is available, and that the prescription requires a licensed practitioner to approve, in which case a practitioner with a license will review the prescription and issue the order to the pharmacy. And if a practitioner, or the decision engine, places a preliminary and follow up liver enzyme lab test on the simulated patient path, then that too is available.

Some embodiments combine the screen aspects as well, such as considering the collaboration interface as the "EHR interface" for the purpose of the other disclosure, such as its FIG. 15 EHR integration.

One possible use case is that a patient can log in at any time, spend as much time learning about (such as through the educational material in FIG. 7 or a similarly placed block without translation) and play with the possibilities (such as through the simulation engine). She may map out an entire course of treatment—an entire lifetime if she wants. And the simulation engine can simulate all of the future consequences, the costs, the pain, the direction, the likelihoods. And then, she may use the practitioner selection features to summon a practitioner—her favorite one, or any other one—to double check her work and make sure that at least the first part of this makes sense. In jurisdictions that require the practitioner to use her license to authorize the patient's treatment, or at least parts of it, she will do so. And so the patient now has an outlet to be the author—or at least an author—of her own treatment, and yet quality can be assured by the eyes double-checking the work. Imagine how liberating this is to a cancer patient, where time spent on the system researching and simulating isn't just doing something to keep busy, but is directly plugged into her treatment. She's not Googling, reading blogs. She's designing her future, taking control over the quality of life decisions.

Let's refer back to a patient in pain, with opioids as a treatment option being considered in its first instance. By being logged into the same system as the practitioner, the practitioner will have difficulties denying the addictive consequence of opioids. The decision engine may announce that additional risk, which the patient will easily see. The physician is not in a position to suppress that information, the way they can now because they are a required, redacting intermediary. For embodiments without a decision engine, the patient may still see the black box warning for the prescription, just as a doctor does. A mistaken practitioner with a belief that the prescription will not be addictive will not likely be able to hand wave and tell the patient to ignore the warnings he sees with his own eyes. Rules can be established to require patient signature as a change order (the change manager's changes) passes by the patient's screen, populated by the system or by the practitioner with that very same warning. The patient can choose to risk addiction if he wants, but the likelihood of being uninformed is significantly reduced by the nature of the embodiments.

Moreover, it should be noted that the flexibility and self-service nature of many uses of the invention as described may allow for the patient to do most of the work that would ordinarily be spent during a traditional encounter with the physician, potentially allowing the physician to dedicate less time to educating the patient and exploring choices with them and more time actually practicing medical decision-making. In other words, it is possible to use this invention to reduce the amount of time doctors spend explaining, thus making each moment with a patient more valuable. One possible employment of this is to provide the practitioners with richer, more satisfying interactions. Another possible use is to increase the practitioner's patient panel size. If practitioners are quality control, and the automated system can handle the majority of the setup and transaction, then practitioners can be employed to supervise and approve a far greater number of patients with the same level of competence as can be done today. Such a disruption has occurred before in medicine, but not before for the bedside practitioners, precisely because of limitations of the currently employed systems. Radiology used to be a one-on-one practice. Then it transitioned to consultative forms, where a radiology reading room was established to cater to an entire medical group's or hospital's needs, thus allowing radiologists to process far more scans and film than before. The disclosed invention may allow for a transition if much of the rest of everyday medicine to the similar consultative role: greater quality at larger panel sizes.

There are many options to address billing, in some embodiments. In some embodiments the patient pays by subscription. In some embodiments the patient pays a fee for use, such as per change or per encounter with a practitioner or per hour with a practitioner. In some embodiments, the patient's insurance is billed. And in some embodiments, a combination occurs, such as ordering payments to reduce the cost to the patient.

Figure 11:
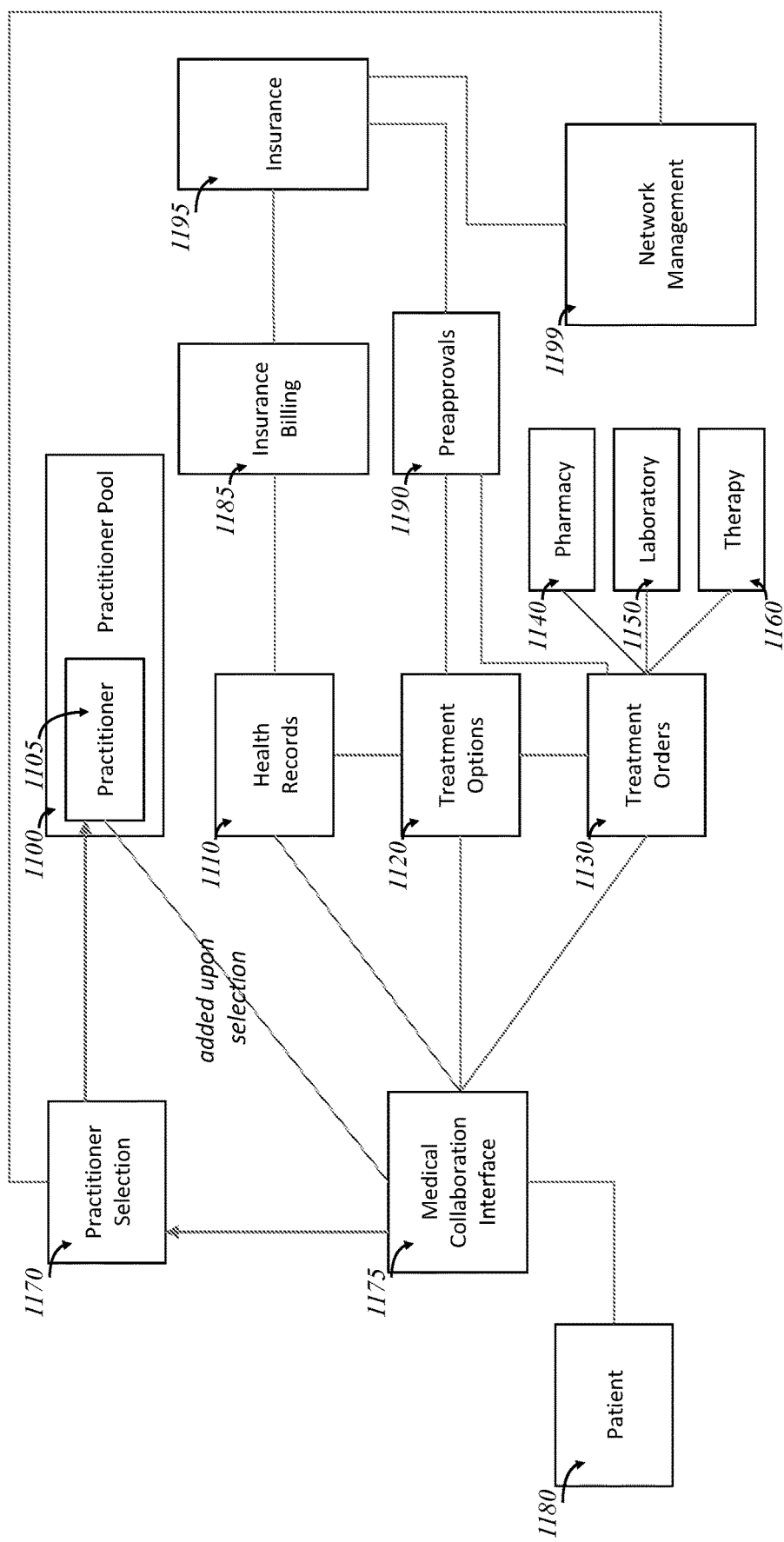
FIG. 11 is a diagram of an embodiment of the invention, extending FIG. 8 by showing an integration into insurance network billing and practitioner selection.

FIG. 11 shows some embodiments with insurance integration. A practitioner selector 1170 communicates with an insurance network manager 1199, to determine which practitioners 1100 are covered in network for which encounters. For example, a practitioner may be a member of the patient's network for primary care, in which case an encounter with the practitioner may be reimbursable by the insurance if that practitioner is selected. In some embodiments, the practitioner selector 1170 will select practitioners, in whole or in part, to reduce the cost to the patient. For example, in one embodiment, where practitioners have unique billing rates per time or per encounter, the selector will select an in-network practitioner who clears her billing rate the best. This allows for an upfront pricing model with insurance included as well, so that the patient can be steered to the best economic costs. This integration of the cost projections as disclosed earlier with insurance allows for a patient to receive total care at an upfront cost. In some embodiments, for practitioners who/which are out of network and balance billing is available, this method allows for the patient to see the balance bill as well and choose accordingly.

The health records are connected to insurance billing in some embodiments. The insurance billing block collects the health records and changes to them that are billable events, and creates standard diagnostic code and procedure code entries for delivery to the insurance entity, in some embodiments. In some embodiments, the EHR requires for treatment orders the CPT codes, and the practitioner selection produces the encounter CPT codes for delivery to billing.

Preapprovals are dispatched from treatment options and treatment orders in some embodiments. The preapprovals block maintains a list from insurance of what procedures require preapproval for this patient. Treatment options that require preapproval are shown with that requirement in some embodiments: ordering the treatment will put the order in abeyance until approval is generated by the preapproval block and delivered to the insurance for approval. In some embodiments, the preapproval block issues an approval request order to preapproval specialists, humans or bots which call the insurance company to collect the approvals and enter the responses in the system. In some embodiments, the practitioners are assigned the preapproval request orders, and they themselves submit the request through the required means of the insurance, in which case they can add that to a billable entry if need be and appropriate.

Figure 12:
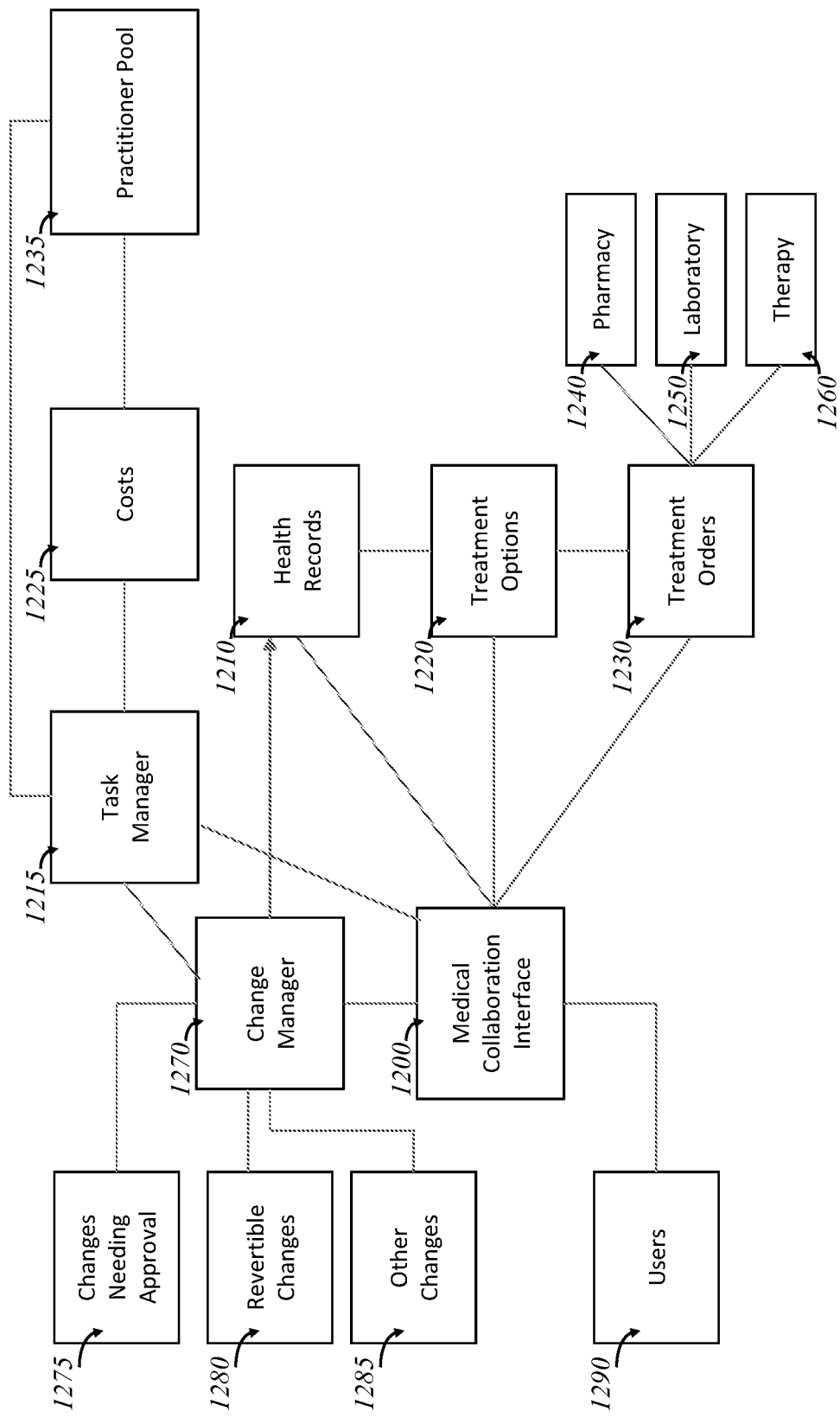
FIG. 12 is a diagram of an embodiment of the invention, showing a task manager interfacing with the costs of practice and a pool of practitioners.

FIG. 12 shows a task manager 1215 in some embodiments. The task manager allows a user 1290 (patient or practitioner) to create projects or tasks, and submit them out to bid. The task manager captures the user's (often the patient's) intended task or project. In some embodiments, the task is described in free-running text. In some embodiments, the task is described as a series of potential changes via the change manager. In some embodiments, the task is described from a database of templates of projects: these projects may be closed-ended such as diagnose sleep apnea, or open ended such as suggest weight loss regimen. The task is then costed, such as by using the expected costs of the practitioners, the treatment options, and template case studies. (In some embodiments, the costs block 1225 is implemented as described for the insurance case above.) In some embodiments, the task costs are finalized directly, and the resources are arranged for and the practitioner(s) is selected from the pool 1255 upon agreement and/or confirmation. In some embodiments, the task is sent out to bid to the practitioner pool, 1225 where the practitioners may bid on them. Further embodiments let the requester view the bids and communicate with the bidders, to determine the scope of work and other items. Upon selection of the bid, the practitioner(s) become introduced into the collaboration interface. In some embodiments, the practitioners offer a cap to their own time and services. In some embodiments, the practitioners offer a cap to all services, in which case the practitioners can become on the hook monetarily for further services such as laboratory: in this case, this operates like a capitation fee scheme. In further embodiments, the capitation is requested from the insurance company, such as upon the patient establishment or upon a bid for services which the practitioner(s) then acquire the capitation from the insurer. In some embodiments, practitioners are not solo but are affiliated with a group practice, for whom the fees or the cap would devolve to. In these cases, the natural transparency of the system prevents any accountable provider from gaming the patients by arguing that a treatment is not available that is available and is to be covered. In cases where the provider becomes unwilling to approve a clearly approvable treatment, the system may allow the patient to call up a second practitioner to approve. In some embodiments a supplemental insurance policy is offered to the patient and integrated into the selection system to cover for corrupt denials: further embodiments provide this insurance by taking a percentage or fixed fee from some or all transactions within the system of this type. In some embodiments, once a task is activated, the change manager 1270 populates the interface 1200 with a template of changes that correspond to at least the initial parts of the treatment or diagnosis regimen.

One further application of the principles and innovations taught here is to return to the problem of robodocs. Automated doctors are not licensed to practice medicine, and most likely cannot nor should not be. However, a similar framework to what was just disclosed for patient directed medicine can be applied more broadly for supervised autonomous medicine. In such uses where practitioners supervise and act as quality control agents for patient direction, substituting the robodoc for the patient leads to robodoc supervision.

Figure 13:
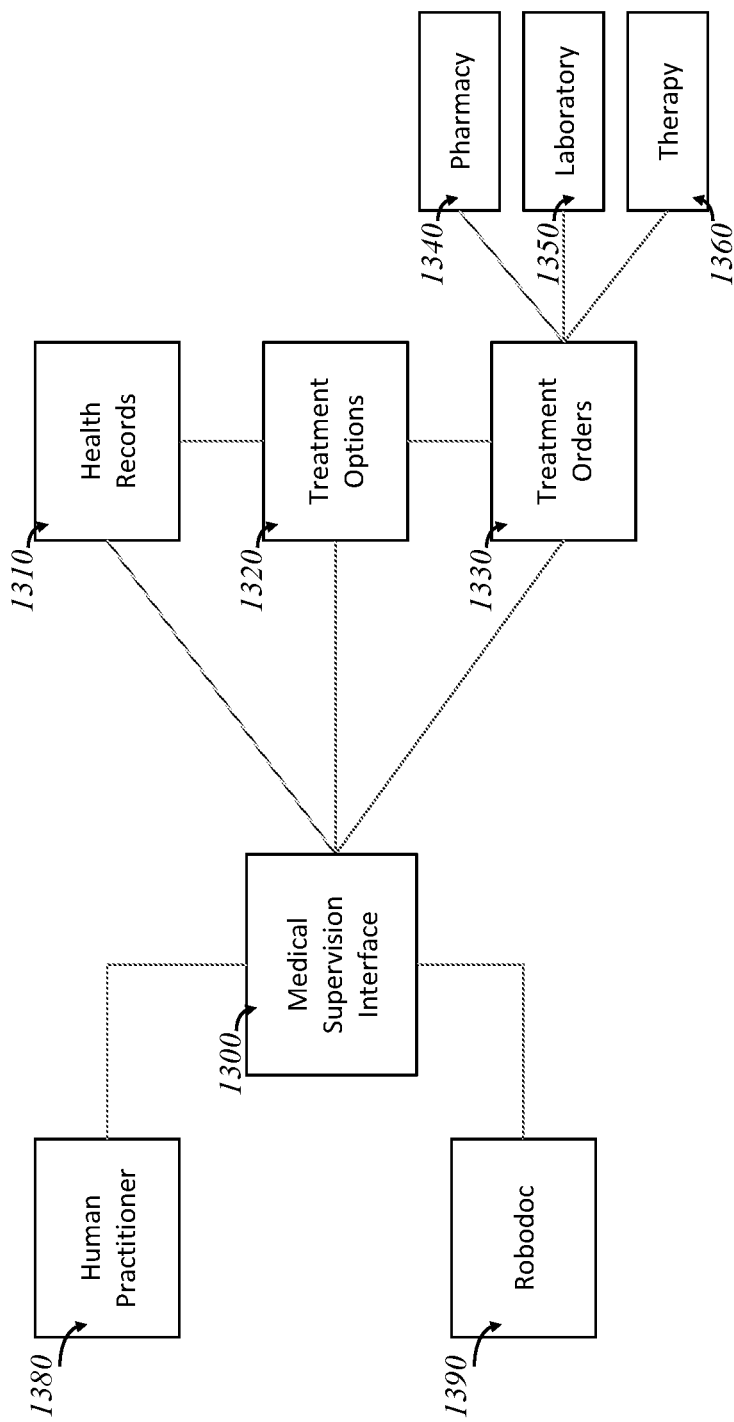
FIG. 13 is a diagram of an embodiment of the invention, showing an automated medical practice engine (robodoc) interfacing with a human practitioner via a medical supervision interface.

FIG. 13 shows an embodiment of robodoc supervision. It is a relabeling of FIG. 5, with the patient removed (optionally) and a human practitioner 1380 interfaced with a robodoc 1390 into what has been relabeled a medical supervision interface 1300. The supervision interface can be the previously disclosed collaboration interface 500, in which case the robodoc must be trained on using the interface. But in some embodiments the interface is further limited so that the robodoc's changes and requests are not done graphically but are communicated semantically or syntactically, such as through an exchange of structured data.

Figure 14:
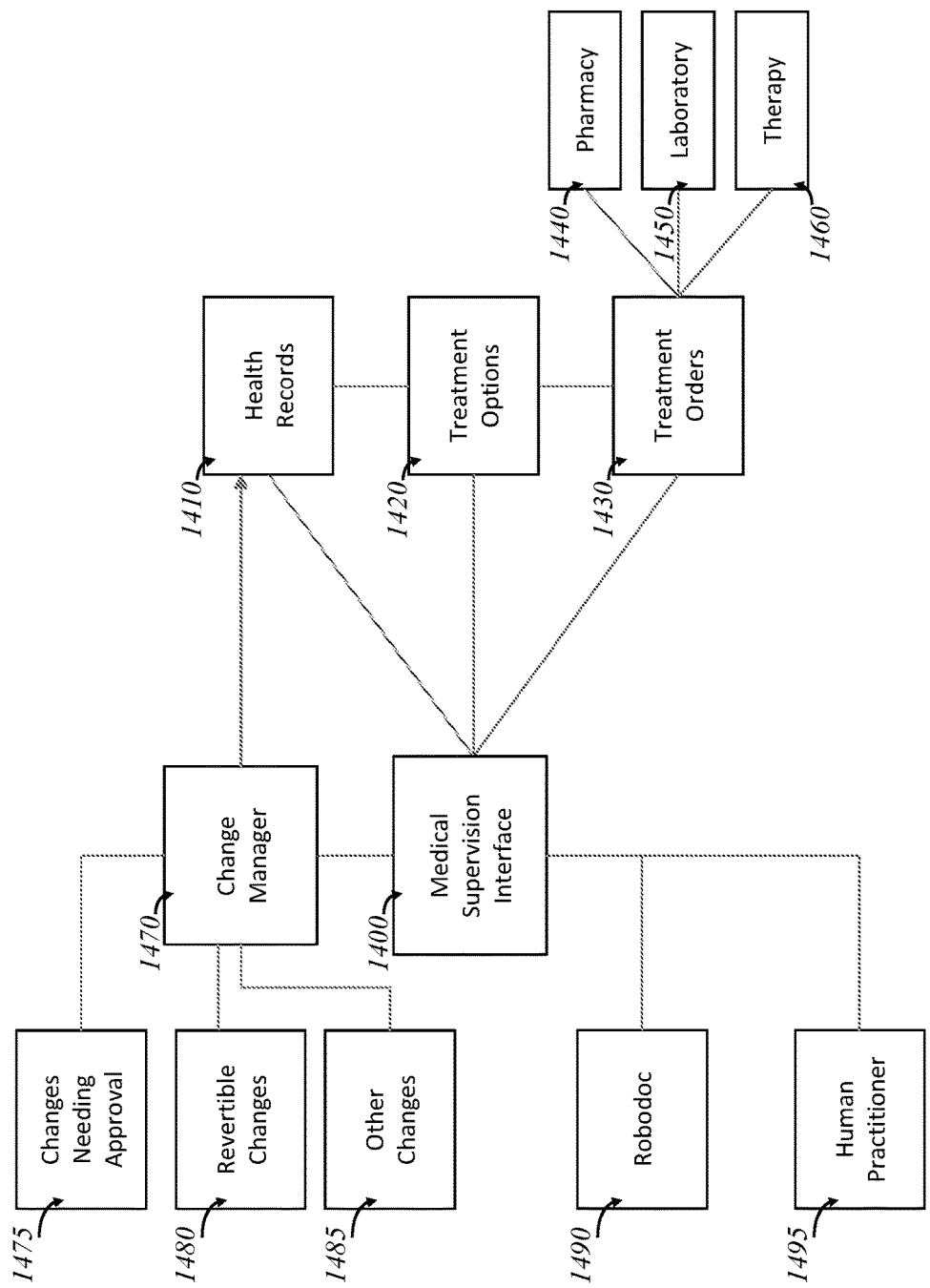
FIG. 14 is a diagram of an embodiment of the invention, showing a change manager and medical supervision interface interacted with by a robodoc and human practitioner.

FIG. 14 shows some embodiments with a robodoc 1490 and a human practitioner (or practitioners) 1495 interfaced into a supervision interface 1400. In these embodiments, the robodoc's work is sent through change management 1470 for review. In some embodiments, the human practitioner is required to approve all orders and changes, thus giving full legal weight to the orders by becoming the human licensee of record for those changes. In other embodiments, the human need only approve a subset. In further embodiments, the contents of the subset are chosen based on the licensure requirements for the orders, the same way as with the patient use cases and embodiments mentioned earlier. As before, the supervision interface can be identical to the collaboration interface, or it may be a reduced form for interaction of the robodoc. Everything mentioned before about change management and approvals can apply here. It's worth mentioning that robodocs are being built to "talk" with patients using human interfaces such as text. This matters because the robodoc can communicate with its supervising practitioner in the same way, if so desired. Thus, the conference in FIG. 6 is in some embodiments carried out between a robodoc and practitioner. For economy, the figures will not be re-included here with the words "Robodoc" replacing patient: it is clear from the specification that such a relabeling represents these further embodiments.

This ability for a licensed human to be the practitioner of record is necessary in many jurisdictions for robodocs to participate in medicine, and doing so electronically as laid out herein allows for the scale increases needed. The leverage a human physician can do by assuring quality of a robodoc but letting the robodoc steer is tremendous.

And of course, the combination of robodoc, supervised human practitioner, and patient are available. The flexibility of the rules engine in some embodiments of the interface and change manager allow for further combination and control. In some embodiments, the robodoc and patient are primarily in communication and the human practitioner is brought in as needed or desired by the patient. In some embodiments, the robodoc is employed more as a concierge, helping the patient weigh the options and making good suggestions but allowing the human practitioner to present differently and with more weight (but with less human practitioner time spent: in many ways, this model is more of a robomedical-assistant than robodoc, but labels are insignificant for that matter).

The collaborative or supervisory aspects of the present invention can be used not just to provide patient-directed medical treatments and care, but to provide a robodoc supervision system that can then be employed even for traditional telemedicine or online medical care.

This disclosure requires familiarity with the state of the art in medical diagnosis and treatment of patients. Terms like "detect" and "infer" are not necessarily absolutes, but may also refer to the increase in a determined value (such as likelihood or probability) or an increase in its confidence. Medical facts, statistical examples, numbers, and the like are for the purposes only of explaining the invention and its operation, and are merely illustrative.

It is the intent in this disclosure to teach not only the pure technological methods but the specific applications to various diseases and conditions.

Throughout this disclosure, multiple specific embodiments are listed that may be extensions of more general embodiments. It is to be understood that the combinations and subprocesses of these embodiments are also taught by this disclosure, as the combinations and subprocesses are able to be anticipated by those skilled in the art upon and only upon reading this disclosure. Furthermore, uses of the plural or the singular do not restrict the number of the item being mentioned: unless explicitly called out as not being so or being logically inconsistent, mentions of singular items are to be construed to also be plural and vice versa.

In the description herein, one or more embodiments of the invention are described, with process steps and functional interactions. Those skilled in the art would realize, after perusal of this application, that embodiments of the invention might be implemented using a variety of other techniques not specifically described, without undue experimentation or further invention, and that such other techniques would be within the scope and spirit of the invention. The use of the words "can" or "may" in regards to the structure and operation of embodiments is to be construed as referring to further embodiments and configuration options, and does not require further experimentation or invention.

The scope and spirit of the invention is not limited to specific examples disclosed therein, but is intended to include the most general concepts embodied by these and other terms.

Although the invention has been described with reference to several exemplary embodiments, it is understood that such descriptions and illustrations are not limiting. Changes may be made within the purview of the appended claims, as presently stated, without departing from the scope and spirit of the invention in its aspects. Although the invention has been described with reference to particular means, materials, machines, and embodiments, the invention is not intended to be limited to the particulars disclosed; rather, the invention extends to all functionally equivalent structures, methods, machines, and uses such as are within the scope of the invention and claims.

This disclosure lists sufficient details to enable those skilled in the art to construct a system around or using the novel methods of the contained inventions, without further discovery or invention.

I claim:

1. A computer-based method comprising:
   a. displaying to a patient and at least one medical practitioner on at least one computer user interface medical treatment options based in at least part on information extracted from an electronic health records system;
b. receiving from said patient a patient-directed tentative treatment orders list chosen from said medical treatment options;
c. filtering said patient-directed tentative treatment orders by which require approval from a medical practitioner;
d. presenting filtered patient-directed tentative treatment orders on said at least one medical practitioner computer user interface;
e. collecting from said at least one medical practitioner for at least one of said filtered patient-directed tentative treatment orders at least in part at least one of: approval without modification, approval with modification, rejection, modifications without approval, and comments;
f. creating confirmed treatment orders from at least in part at least one of approved filtered patient-directed tentative treatment orders, and tentative treatment orders that do not require approval;
g. applying treatments contained in said treatment orders record to the patient,
wherein said presenting, receiving, collecting, filtering, and creating are performed by one or more computers.

2. The method of claim 1 comprising further steps of associating said treatment options with the degree to which the patient's medical insurance provides coverage for said options, and displaying said associations.

3. The method in claim 1 comprising further step of connecting said user interfaces to a collaboration interface for creating and editing patient-directed tentative treatment orders.

4. The method in claim 3 wherein said collaboration interface possesses in part a remotely viewed shared visual interface.

5. The method in claim 3 wherein said collaboration interface is associated with a real-time digital conferencing system wherein said patient and at least one of said at least one medical practitioner may conference while using said collaboration interface.

6. The method in claim 3 comprising further step of providing a change manager for at least one of—health records, treatment options, and treatment orders—to said collaboration interface, wherein users may track changes, approvals, and areas of collaboration.

7. The method of claim 1 comprising further steps of determining that a patient-directed treatment option requires approval from a licensed medical practitioner, directing a licensed medical practitioner to approve of said patient-directed treatment option, and entering said licensed medical practitioner as a licensed medical practitioner of record for the treatment.

8. The method of claim 1 comprising further steps of:
selecting at least one selected medical practitioner from a pool of available practitioners wherein the selection is made at least in part it at least one of: the identity of said treatment option, the prior relationship between said selected medical professional, and the availability of said selected medical professional.

9. The method of claim 1 comprising further step of providing to at least one user access to at least one of—a risk profiler, and a simulation and decision engine—that allows the user to explore in real-time the likelihoods and possible future consequences of medical decisions.

10. The method of claim 1 comprising further step of performing translation of medical terminology from said user interface for said patient, wherein said translation may be chosen to facilitate easier comprehension.

11. A computer-based treatment order entry system comprising:
a. an electronic health records subsystem;
b. a patient user interface and at least one medical practitioner user interface, wherein a selectable list of available and orderable medical treatment options is displayed, produced in at least part from said electronic health records and displayed on said patient user interface;
c. an electronically stored list of patient-directed tentative treatment orders, chosen on said patient user interface by the patient from said selectable list of available and orderable medical treatment options;
d. a filter which produces a subset of said patient-directed tentative treatment orders which require approval from a medical practitioner;
e. a collector which operates on said medical practitioner user interface and collects from said at least one medical practitioner of at least one of said filtered patient-directed tentative treatment orders at least in part at least one of: approval without modification, approval with modification, rejection, modifications without approval, and comments;
f. an electronic record of treatment orders created at least in part from at least one of: said approvals list, and said patient-directed tentative treatment orders that do not require approval; wherein the treatments within said treatment orders record are applied to the patient.

12. The system of claim 11 wherein said treatment options are associated with the degree to which the patient's medical insurance provides coverage for said options.

13. The system in claim 11 further comprising a collaboration interface for creating and editing patient-directed tentative treatment orders between said patient and said at least one medical practitioner, wherein said patient and said at least one medical practitioner become collaboration interface users.

14. The system in claim 13 wherein said collaboration interface possesses in part a remotely viewed shared visual interface.

15. The system in claim 13 wherein said collaboration interface is associated with a real-time digital conferencing system wherein said patient and at least one of said at least one medical practitioner may conference while using said collaboration interface.

16. The system in claim 13 comprising further a change manager presented upon said collaboration interface for at least one of—health records, treatment options, and treatment orders—wherein users may track changes, approvals, and areas of collaboration.

17. The system of claim 11 wherein said disposition collector determines whether a patient-directed treatment option requires approval from a licensed medical practitioner, directs a licensed medical practitioner to approve of said patient-directed treatment option, and enters said licensed medical practitioner as a licensed medical practitioner of record for the treatment.

18. The system of claim 11 comprising further a practitioner selector which selects at least one selected medical practitioner from a pool of available practitioners wherein the selection is made at least in part it at least one of: the identity of said treatment option, the prior relationship between said selected medical professional, and the availability of said selected medical professional.

19. The system of claim 11 comprising further at least one of—a risk profiler, and a simulation and decision engine—that allows the user to explore in real-time the likelihoods and possible future consequences of medical decisions.

20. The system of claim 11 comprising further a lay translator that performs translation of medical terminology from said digital interface for said patient, wherein said translation may be chosen to facilitate easier comprehension.

* * * * *